(12) United States Patent
Osypka et al.

(10) Patent No.: US 8,562,538 B2
(45) Date of Patent: *Oct. 22, 2013

(54) SYSTEM FOR DETERMINING THE LEFT-VENTRICULAR EJECTION TIME TLVE OF A HEART OF A SUBJECT

(75) Inventors: Markus J. Osypka, Knuellwald (DE); Donald P. Bernstein, Rancho Santa Fe, CA (US)

(73) Assignee: Osypka Medical GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,591

(22) Filed: Mar. 7, 2011

(65) Prior Publication Data

US 2011/0190601 A1   Aug. 4, 2011

Related U.S. Application Data

(62) Division of application No. 11/386,422, filed on Mar. 22, 2006, now Pat. No. 7,904,141, which is a division of application No. 10/267,313, filed on Oct. 9, 2002, now Pat. No. 7,822,470.

(60) Provisional application No. 60/328,694, filed on Oct. 11, 2001.

(51) Int. Cl.
A61B 5/00   (2006.01)

(52) U.S. Cl.
USPC ............................ 600/526; 600/513; 600/301

(58) Field of Classification Search
USPC .......................................... 600/526, 301, 513
See application file for complete search history.

(56) References Cited

U.S. PATENT DOCUMENTS 1,908,688 A   5/1933   Call 2,327,874 A   8/1943   De Jong
3,284,724 A   11/1966   Marlow
3,340,867 A   9/1967   Kubicek et al.

(Continued)

FOREIGN PATENT DOCUMENTS

| DE | 199 14 437 | 10/2000 |
|---|---|---|
| EP | 0 480 078 | 4/1992 |
| EP | 1 754 441 B1 | 1/2008 |
| GB | 618405 | 2/1949 |

OTHER PUBLICATIONS

Wallace, Arthur W.; "Endotracheal Cardiac Output Monitor"; Anesthesiology; vol. 92; 178-89; Jan. 2000.

(Continued)

*Primary Examiner* — Niketa Patel
*Assistant Examiner* — Alyssa M Alter
(74) *Attorney, Agent, or Firm* — Martin & Ferraro, LLP

(57) ABSTRACT

In order to reliably determine the left-ventricular ejection time $T_{LVE}$ of a heart of a subject, at least two different measuring methods are employed. This includes in any case the derivation of a first waveform related to thoracic electrical bioimpedance or bioadmittance. A second waveform can be determined by using pulse oximetry, Doppler velocimetry, measurement of arterial blood pressure and measurement of peripheral electrical bioimpedance or bioadmittance. Depending on signal quality, the results obtained by each method are weighted and then averaged. The weighted average for left-ventricular ejection time is used as an input variable for cardiovascular monitoring methods, which determine objective measurements of cardiovascular function and performance. Such measurements include, but are not limited to, left ventricular ejection fraction, stroke volume, cardiac output, systolic time ratio, and indices of ventricular contractility.

8 Claims, 14 Drawing Sheets

(56) References Cited

U.S. PATENT DOCUMENTS

| | | |
|---|---|---|
| 3,402,572 A | 9/1968 | Chase et al. |
| 3,601,126 A | 8/1971 | Estes |
| 3,971,365 A | 7/1976 | Smith |
| 4,001,554 A | 1/1977 | Hall et al. |
| 4,057,736 A | 11/1977 | Jeppson |
| 4,168,459 A | 9/1979 | Roesel, Jr. |
| 4,207,772 A | 6/1980 | Stoller |
| RE30,750 E | 9/1981 | Diack et al. |
| 4,289,142 A | 9/1981 | Kearns |
| 4,354,501 A | 10/1982 | Colley et al. |
| 4,387,722 A | 6/1983 | Kearns |
| 4,416,277 A | 11/1983 | Newton et al. |
| 4,450,527 A | 5/1984 | Sramek |
| 4,504,882 A | 3/1985 | Breton |
| 4,509,526 A | 4/1985 | Barnes et al. |
| 4,562,843 A | 1/1986 | Djordjevich et al. |
| 4,807,638 A | 2/1989 | Sramek |
| 4,836,214 A | 6/1989 | Sramek |
| 4,850,361 A | 7/1989 | Maekawa |
| 4,858,614 A | 8/1989 | Stevens et al. |
| 4,953,556 A | 9/1990 | Evans |
| 5,052,395 A | 10/1991 | Burton et al. |
| 5,103,828 A * | 4/1992 | Sramek .................. 600/481 |
| 5,178,151 A | 1/1993 | Sackner |
| 5,178,154 A | 1/1993 | Ackmann et al. |
| 5,188,106 A | 2/1993 | Nappholz et al. |
| 5,241,964 A | 9/1993 | McQuilkin |
| 5,280,429 A | 1/1994 | Withers |
| 5,309,917 A | 5/1994 | Wang et al. |
| 5,311,878 A | 5/1994 | Brown et al. |
| 5,316,004 A | 5/1994 | Chesney et al. |
| 5,423,326 A | 6/1995 | Wang et al. |
| 5,443,073 A | 8/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,642,734 A | 7/1997 | Ruben et al. |
| 5,685,316 A | 11/1997 | Schookin et al. |
| 5,782,774 A | 7/1998 | Shmulewitz |
| 5,791,349 A | 8/1998 | Shmulewitz |
| 6,016,445 A | 1/2000 | Baura |
| 6,058,325 A | 5/2000 | Baura |
| 6,095,987 A | 8/2000 | Shmulewitz et al. |
| 6,102,869 A | 8/2000 | Meier et al. |
| 6,161,038 A | 12/2000 | Schookin et al. |
| 6,169,914 B1 | 1/2001 | Hovland et al. |
| 6,186,955 B1 | 2/2001 | Baura |
| 6,198,972 B1 | 3/2001 | Hartlaub et al. |
| 6,238,349 B1 | 5/2001 | Hickey |
| 6,263,243 B1 | 7/2001 | Lang |
| 6,275,012 B1 | 8/2001 | Jabaji |
| 6,292,377 B1 | 9/2001 | Sasaki |
| 6,316,518 B1 | 11/2001 | Phipps et al. |
| 6,334,849 B1 | 1/2002 | Sunagawa |
| 6,336,045 B1 | 1/2002 | Brooks |
| 6,404,089 B1 | 6/2002 | Tomion |
| 6,442,422 B1 | 8/2002 | Duckert |
| 6,490,474 B1 | 12/2002 | Willis et al. |
| 6,494,832 B1 | 12/2002 | Feldman et al. |
| 6,511,438 B2 | 1/2003 | Bernstein et al. |
| 6,633,777 B2 | 10/2003 | Szopinski |
| 6,641,520 B2 | 11/2003 | Bailey et al. |
| 7,186,219 B2 | 3/2007 | Osypka et al. |
| 7,822,470 B2 | 10/2010 | Osypka et al. |
| 7,904,141 B2 | 3/2011 | Osypka et al. |
| 2003/0052564 A1 | 3/2003 | Wilsdorf |
| 2003/0206021 A1 | 11/2003 | Laletin et al. |
| 2004/0143297 A1 | 7/2004 | Ramsey |
| 2004/0152996 A1 | 8/2004 | Gersing |
| 2005/0012414 A1 | 1/2005 | Gersing |
| 2007/0043303 A1 | 2/2007 | Osypka et al. |

OTHER PUBLICATIONS

Lababidi, Z., et al; "The First Derivative Thoracic Impedance Cardiogram"; Circulation; vol. XLI: cover page and pp. 651-658; Apr. 1970.

Weissler, A., et al; "Systolic Time Intervals in Heart Failure in Man"; Circulation; vol. XXXVII: cover page and pp. 149-159; Feb. 1968.

Spitaels, S., et al.; "The Influence of Heart Rate and Age on the Systolic and Diastolic Time Intervals in Children"; Circulation; vol. XLIX: cover page and pp. 1107-1115; Jun. 1974.

Bleicher, W et al; "Automatic Device for Noninvasive Monitoring of Stroke Volume, Cardiac Output, Systolic Time Intervals, and Derived Hemodynamic Parameters"; Computers in Cardiology; pp. 419-422; Oct. 22, 1980.

European Patent Office, European search report, Application No. EP 05017871, Nov. 2, 2005, 4 pages.

* cited by examiner

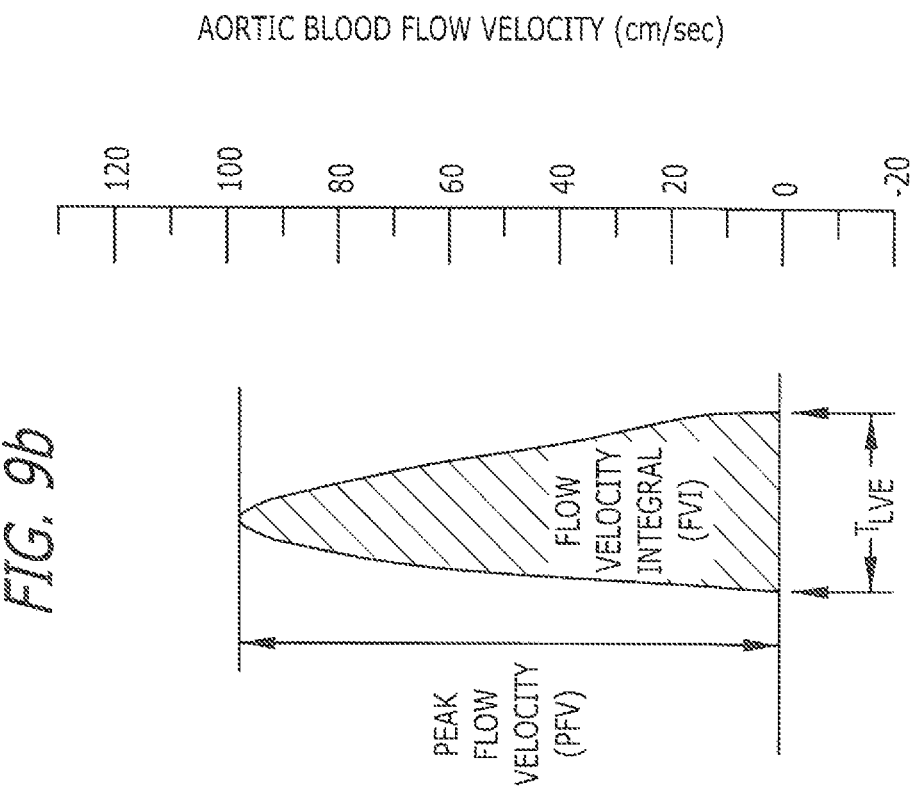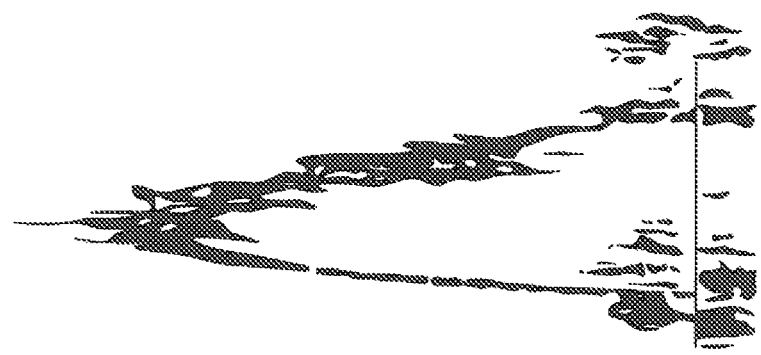

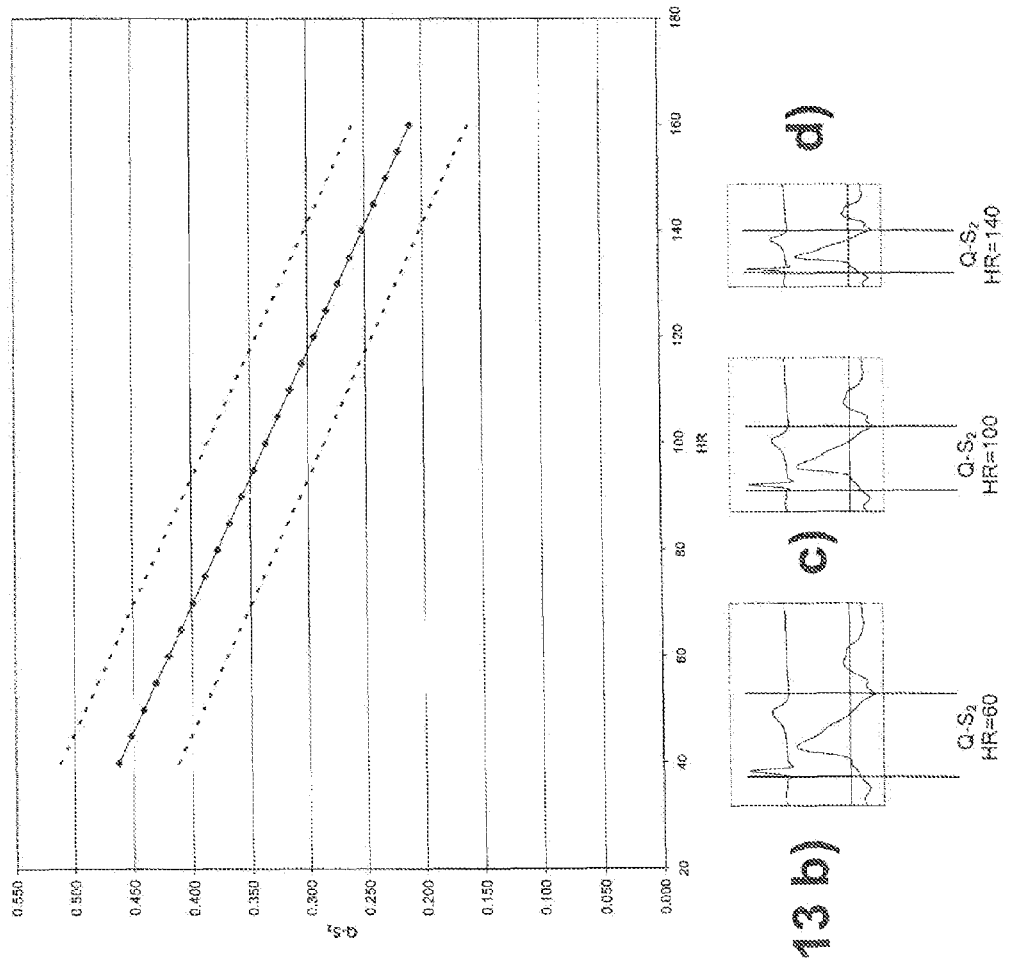

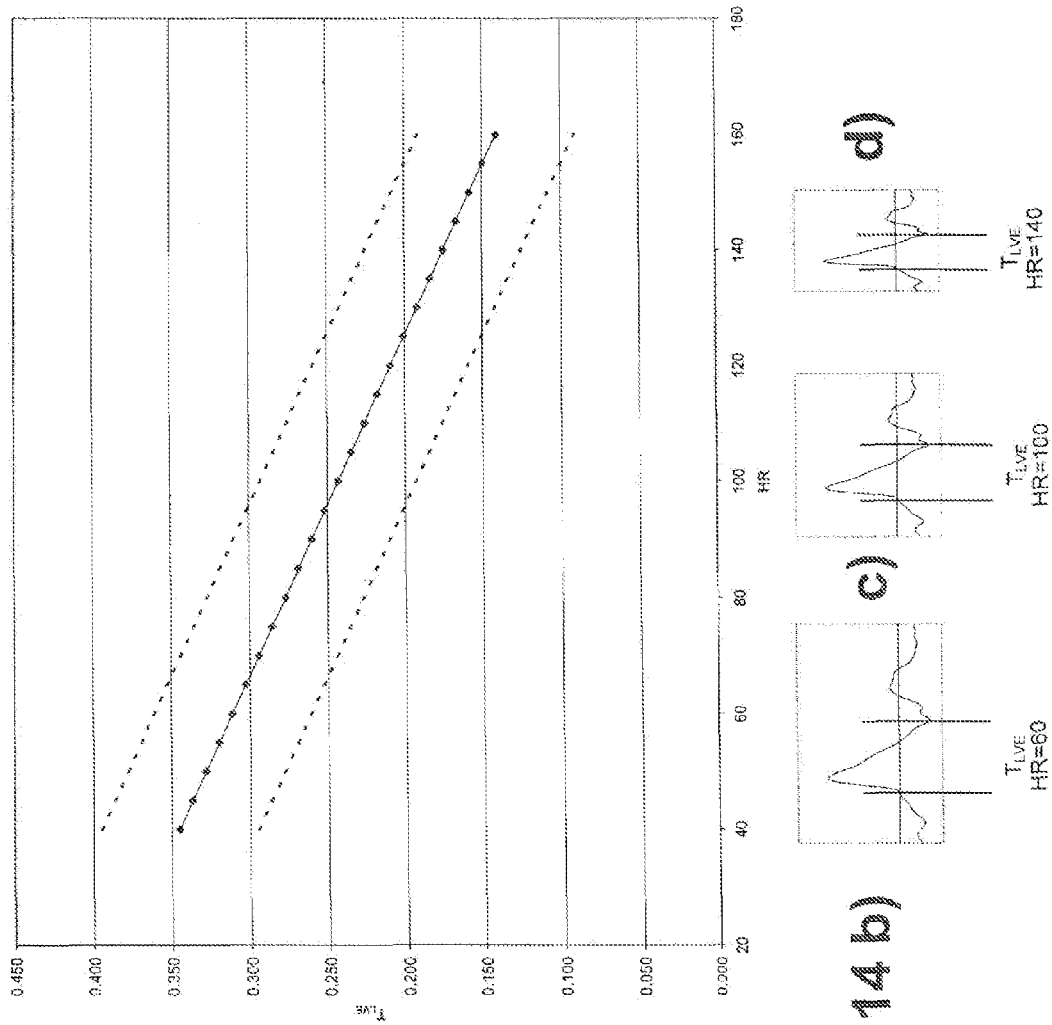

SYSTEM FOR DETERMINING THE LEFT-VENTRICULAR EJECTION TIME TLVE OF A HEART OF A SUBJECT

This application is a divisional of U.S. application Ser. No. 11/386,422, filed Mar. 22, 2006 (now U.S. Pat. No. 7,904,141); which is a divisional of U.S. application Ser. No. 10/267,313, filed Oct. 9, 2002 (now U.S. Pat. No. 7,822,470); which claims the benefit of U.S. Provisional Application No. 60/328,694, filed Oct. 11, 2001; all of which are incorporated herein by reference.

BACKGROUND OF THE INVENTION

1. Field of the Invention

The present invention relates to a method and an apparatus for determining the left-ventricular ejection time $T_{LVE}$ of a heart of a subject.

$T_{LVE}$ is the temporal interval defining the mechanical period for ejection of blood from the left ventricle of a subject's heart. $T_{LVE}$ temporally refers to the ejection phase of mechanical systole. $T_{LVE}$ commences with opening of the aortic valve, and ends with aortic valve closure. The accurate measurement of $T_{LVE}$ is of paramount importance in the calculation of left ventricular stroke volume, cardiac output, and systolic time ratio.

Stroke volume (SV), and specifically left ventricular SV, is the quantity of blood ejected from the left ventricle into the aorta over $T_{LVE}$, or the ejection phase of mechanical systole, over one cardiac cycle, or heart beat. Cardiac output (CO) is the quantity of blood ejected from the left ventricle per minute, i.e., depends on SV and heart rate (HR). HR is the number of heartbeats per minute. CO is the product of SV and HR, i.e., $$CO=SV \cdot HR.$$

Accurate, serial, quasi, or non-static determinations of SV, and thus, CO, are rigidly dependent on the accurate measurement of $T_{LVE}$.

2. Description of the Related Art

In the related art, $T_{LVE}$ was derived from curves obtained by measurements of a thoracic electrical bioimpedance or bioadmittance (TEB). In young, healthy individuals, the measurement of TEB results in waveforms that routinely exhibit, and readily permit, identification of the opening of the aortic valve (point "B") and its closure (point "X") by visual inspection. However, in various states and degrees of cardiopulmonary pathology, point "X" is commonly obscured or absent, see Lababidi Z, Ehmke D A, Durnin R E, Leaverton P E, Lauer R M.: The first derivative thoracic impedance cardiogram. Circulation 1970; 41: 651-658. These are, unfortunately, the situations where accurate $T_{LVE}$ measurements are mandatory.

In a further advanced method, simultaneous electronic registration of the first time-derivative of the cardiac-related impedance change waveform generated by TEB, and the mechanically generated heart sounds obtained via phonocardiography, were employed for determination of $T_{LVE}$, and specifically, aortic valve closure (first high frequency registration of the second heart sound). Unfortunately, the technique of phonocardiography is cumbersome, sensitive to motion and ventilation artifacts (low signal-to-noise ratio), and is unsuited for routine clinical application.

To the present time, alternative methodology is limited to frequency spectrum domain analysis (Wang et al., U.S. Pat. Nos. 5,443,073; 5,423,326; 5,309,917) and to the establishment of temporal "expectation windows" for predictive estimation of periodic landmark occurrences, namely, aortic valve closure, and the duration between such landmarks, namely, $T_{LVE}$.

Regarding the latter method, Weissler et al. (Weissler A M, Harris W S, Schoenfeld C D. Systolic time intervals in heart failure in man. Circulation 1968; 37: 149-159, incorporated herein by reference) empirically determined, with heart rate as the variable, regression equations for the temporal interval defining and predicting electromechanical systole (known as "$QS_2$") and the subordinate time intervals contained within, comprising, in particular, the left ventricular flow, or ejection time $T_{LVE}$. Bleicher et al. (Bleicher W, Kemter B E, Koenig C. Automatische kontinuierliche Vermessung des Impedanzkardiogramms. Chapter 2.6 In: Lang E, Kessel R, Weikl A [eds.]. Impedanz-Kardiographie. Verlag C M Silinsky, Nürnberg, Paris, London 1978) compares the regression equations reported by Weissler with those of other investigators (Spitaels S. The influence of heart rate and age on the systolic and diastolic time intervals in children. Circulation 1974; 49: 1107-1115. Kubicek W G. The Minnesota impedance cardiograph. Theory and applications. Biomed Engineering September 1974.) Weissler remains the "gold standard" within the statistical-based methods. With temporal reference to the electrocardiogram and the predetermined temporal occurrence of aortic valve opening obtained by an alternative method, these regression equations predict time intervals which can then be used to estimate the magnitude of $T_{LVE}$ and, thus, the temporal occurrence of aortic valve closure. A time-predictive expectation window can be bracketed around a predicted occurrence of aortic valve closure to confirm the point of measured aortic valve closure assessed by an alternative method.

However, the application of an expectation window, employed as the only alternative method for determining $T_{LVE}$, is based on error prone, statistical methods. While correlation (the closeness of association) between the regression equations and measured values of $T_{LVE}$ is clinically acceptable, time-predictive expectation windows inherently possess unacceptably large standard deviations due to individual biologic variability. In contradistinction, inherently accurate, alternative, objective measurements of $T_{LVE}$ are limited in accuracy solely by the precision of the measurement device, which is presupposed to have a much smaller error of the estimate. Thus, time-predictive expectation windows have only limited validity within a single, discreet cardiac cycle. Moreover, the predictive accuracy further deteriorates in the presence of cardiac rhythms, which are not of regular sinus origin. In the presence of irregularly, irregular chaotic rhythms of supraventricular origin, such as atrial fibrillation with variable ventricular response, or other irregular supraventricular tachydysrhythmias, the use of time-predictive expectation windows are rendered virtually all but useless. In the presence of sinus or pathologic supraventricular rhythms, coexisting with electrical systoles generated from ventricular origins, known as premature ventricular contractions, accurate assessment of mean values for $T_{LVE}$ based on time-predictive expectation windows is impossible.

SUMMARY OF THE INVENTION

It is an object of the present invention to provide a method and an apparatus for determining the left-ventricular ejection time $T_{LVE}$ of a heart of a subject more reliably, in particular in those situations in which the determination of $T_{LVE}$ with the related art methods is insufficient, namely in some states of cardiopulmonary pathology.

According to the invention, the measurement of the thoracic electrical bioimpedance or thoracic electrical bioadmittance (TEB) is used for deriving a waveform from which the left-ventricular ejection time can be determined. However, in addition to that method, at least a second waveform is derived. For the derivation of this second waveform, the present invention offers a variety of different methods. These methods include, but are not limited to a) the continuous extrapolation of arterial blood oxygen saturation ($SpO_2$) values by means of pulse oximetry, b) the use of Doppler velocimetry, in particular $b_1$) the use of Doppler velocimetry applied to the esophagus, and/or $b_2$) the use of Doppler velocimetry applied to the radial artery, c) the measurement of arterial blood pressure, in particular $c_1$) the continuous invasive measurement of arterial blood pressure, and/or $c_2$) the continuous noninvasive measurement of arterial blood pressure (applanation tonometry, or sphygmocardiography).

Each of these methods can provide continuous waveforms with characteristic patterns related to either an arterial pressure or flow pulse wave.

Each method, when applied, determines $T_{LVE}$, beat-by-beat. Ideally, a signal processor receives the continuous waveforms provided by each method in parallel, performs synchronization in time, and then determines a "method averaged", or "final", $T_{LVE}$. The contribution of each method applied depends on the level of acceptable signal quality. In the preferred embodiment, each method's contribution to the "method averaged" $T_{LVE}$ is weighted, based on the level of acceptable signal quality. The weights can be fixed, i.e., predetermined, or also can be adapted depending on signal quality parameters, such as the noise level.

Alternatively, the "method-averaged" $T_{LVE}$ is determined by identifying "common" points in time for opening and closure of the aortic valve, which requires that all waveforms are exactly aligned synchronously with time.

In order to further improve the inventive method, an expectation window for $T_{LVE}$ can be established by using a regression equation, prior to precisely determining $T_{LVE}$. The latter improvement is in particular useful in those cases wherein the determination of aortic valve closure from the waveform is ambiguous.

In order to make use of the inventive method, the invention provides a system suited to perform some of the various methods mentioned above but need not apply to each method. In a preferred version of the invention, the system is suited to perform three different of the above-mentioned methods, i.e., the thoracic electrical bioimpedance/bioadmittance measurement (TEB) and two additional methods.

The apparatus according to the invention can be tailor-made for the respective application in which the apparatus is to be used. In many cases, a combination of an apparatus for obtaining a thoracic electrical bioimpedance/bioadmittance (TEB) waveform and a pulse oximeter is sufficient.

For an anesthesiologist, a combination of a TEB apparatus and a Doppler velocimeter is preferred. In this case, the thoracic electrical bioimpedance or bioadmittance is measured by electrodes placed on a catheter, or probe, which is adapted to be inserted into the esophagus. An ultrasound crystal being part of a Doppler velocimeter also is incorporated into the catheter, or probe. The trunk of a patient under anesthesia is often covered with sterile blankets. The patient's head remains the only part of the upper body being easily accessible. Hence, the practical approach to obtain waveforms from which $T_{LVE}$ can be derived is inserting a catheter, or probe, into the patient's esophagus. The apparatus tailored for the anesthesiological applications can, as a third unit, also includes a pulse oximeter having a probe attached to a patient's finger or toe, because, in a lot of cases, the hand or the foot of the patient subject also is readily accessible.

For a doctor investigating the vasculature, for example, in a hypertension clinic, an apparatus including a bioimpedance analyzer, a pulse oximeter and other methods accessing the "peripheral" blood pressure is ideally suited. In this context, a peripheral method is defined as method which can be applied to an extremity (limb) of a patient. Peripheral methods include Doppler velocimetry applied to the radial artery, and the invasive measurement of arterial blood pressure, wherein a sensor is inserted into an artery of an extremity of a patient. Alternatively, applanation tonometry or sphygmocardiography can be used.

The inventive system is not limited to the above examples. In particular, other combinations are imaginable, as long as TEB is used. Furthermore, a system is part of the invention which includes any of the above-mentioned methods or devices, such that the system can be used in a variety of different fields and applications.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 9a shows a raw signal obtained from esophageal Doppler velocimetry during mechanical systole.

FIG. 9b shows the signal of FIG. 9a after smoothing (filtering). It graphically demonstrates the method how TLVE is extracted from the Doppler velocity waveform.

FIG. 13a illustrates the method by which a time domain is constructed for predicting the temporal occurrence of aortic valve closure.

FIG. 13b illustrates the Q-$S_2$ interval at a heart rate of 60 bpm, shown within a cardiac cycle of the ECG and corresponding rate of change of impedance waveform.

FIG. 13c illustrates the Q-$S_2$ interval at a heart rate of 100 bpm, shown within a cardiac cycle of the ECG and corresponding rate of change of impedance waveform.

FIG. 13d illustrates the Q-$S_2$ interval at a heart rate of 140 bpm, shown within a cardiac cycle of the ECG and corresponding rate of change of impedance waveform.

FIG. 14a illustrates the method by which an expectation window is established for predicting the $T_{LVE}$.

FIG. 14b illustrates $T_{LVE}$ at a heart rate of 60 bpm, shown within a cardiac cycle of the ECG and corresponding rate of change of impedance waveform.

FIG. 14c illustrates $T_{LVE}$ at a heart rate of 100 bpm, shown within a cardiac cycle of the ECG and corresponding rate of change of impedance waveform.

FIG. 14d illustrates $T_{LVE}$ at a heart rate of 140 bpm, shown within a cardiac cycle of the ECG and corresponding rate of change of impedance waveform.

DETAILED DESCRIPTION OF THE DRAWINGS

Reference will now be made in detail to the present preferred embodiments (exemplary embodiments) of the invention, an examples of which are illustrated in the accompanying drawings. Wherever possible, the same reference numbers will be used throughout the drawings to refer to the same or like parts.

Figure 1:
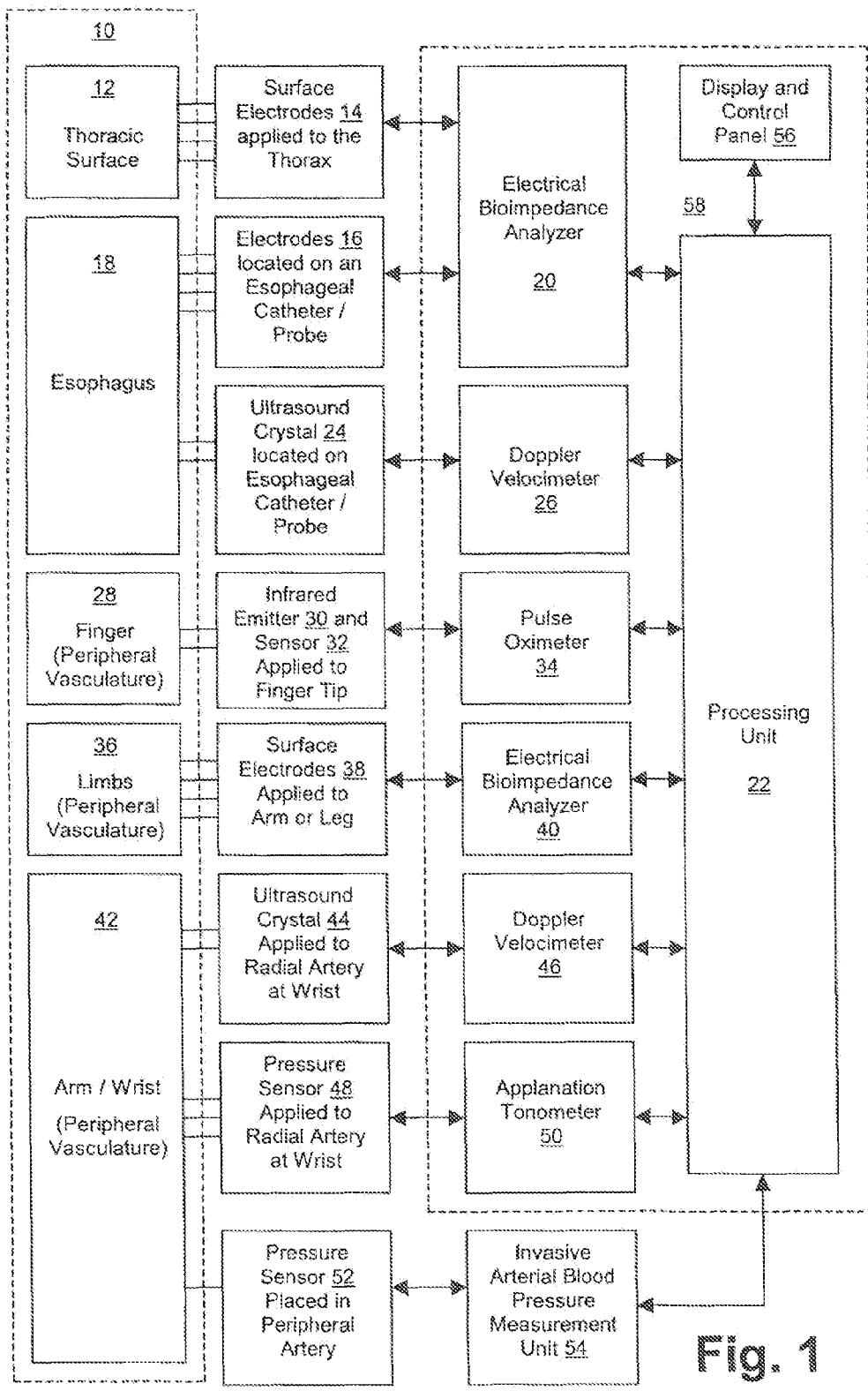
FIG. 1 schematically shows a system/apparatus according to one embodiment of the present invention, and its electrical interfaces with a subject.

FIG. 1 schematically shows a system according to the present invention, and its electrical interfaces with a subject 10. A dashed line indicates the subject's areas of interest to which an apparatus according to this invention can be applied.

The measurement of thoracic electrical bioimpedance (or bioadmittance), which is part of all embodiments of the present invention, is performed by one of the two different methods: In the first, more commonly used method, surface electrode arrays 14 are applied to the thorax of the subject. For example, tetrapolar arrays of spot electrodes are placed on each side of the neck and on each side of the lower part of the thorax, at the level of the xiphoid process. Alternatively, electrodes are located on an esophageal catheter, or probe 16, and this catheter, or probe 16, is inserted into the esophagus 18. Either surface electrode arrays, or the electrodes for the esophageal catheter, or probe, are connected to an electrical bioimpedance (or bioadmittance) analyzer 20. The preferred apparatus for measurement of bioimpedance, or bioadmittance, and the corresponding electrode montage of electrode arrays, are described and shown in U.S. patent application Ser. No. 09/824,942 [Bernstein/Osypka] incorporated herein by reference. The bioimpedance, or bioadmittance, measuring apparatus 20 applies a low amplitude, high frequency alternating current (AC) through the outer electrodes, measures a corresponding voltage drop between the inner electrodes, and calculates the bioimpedance, or bioadmittance. Hence, if the bioimpedance is determined, the measured voltage magnitude is divided by the applied current sent through the electrodes, and electrical bioimpedance analyzer 20 processes a continuous impedance signal $$Z(t)=Z_0+\Delta Z(t),$$

comprising of a quasi-constant offset, $Z_0$, or base impedance, and a pulsatile component, $\Delta Z(t)$, related to the cardiac cycle.

In this context, "continuous" presupposes that this waveform contains a stream of discrete, digital samples, and, thus, is not limited to a truly continuous, analog waveform.

The continuous $\Delta Z$ waveform, which can be considered as an image of an aortic blood flow signal superimposed on an aortic volume change signal, is transferred to a processing unit 22, along with the simultaneously obtained value for the base impedance $Z_0$.

By the apparatuses mentioned above, a first waveform can be derived from which a first value for the left-ventricular ejection time $T_{LVE}$ can be determined.

The system according to the invention offers a vast variety of possibilities for deriving at least one second waveform from which $T_{LVE}$ can also be determined.

A first one of these possibilities relates to determining the blood flow velocity in the aorta. To this end, an esophageal catheter/probe, with an ultrasound crystal sensor 24 incorporated at the tip, is placed into the subject's esophagus 18. In the event that the electrodes for the bioimpedance measurements are placed on a catheter/probe, the same catheter can be used both for the bioimpedance measurement and for Doppler velocimetry. Ultrasound crystal sensor 24 is connected to a Doppler velocimeter 26. Doppler velocimeter 26 transfers a continuous voltage, corresponding to aortic velocity, to processing unit 22.

Another possibility for deriving a second curve is pulse oximetry. The subject's area of interest is here a finger or toe 28 (the peripheral vasculature). For obtaining signals, an infrared emitter 30 as well an infrared sensor 32 are applied to the fingertip or toe. The data obtained by sensor 32 are sent to a pulse oximeter 34. The latter transfers an oxygen saturation waveform (which is continuously obtained) to processing unit 22.

Another apparatus also measures the electrical bioimpedance. However, it is not the bioimpedance across the thorax of the subject. Rather, an impedance signal obtained at the limbs 36 (the peripheral vasculature) of the subject is used to measure a second waveform from which $T_{LVE}$ can be derived. To this end, an array of four surface electrodes 38 are applied to an arm or a leg of the subject. As in the case of the measurement of the thoracic electrical bioimpedance, an alternating current (AC) source applies a low amplitude, high frequency current through the outer electrodes, and a voltage drop is measured by a voltmeter between the inner electrodes. Alternatively, an array of two surface electrodes is utilized, using each electrode for current application and voltage sensing. The data are processed in an electrical bioimpedance analyzer 40 which is also connected to processing unit 22.

Three further methods that may be incorporated into the apparatuses of certain embodiments of the present invention are directed towards the peripheral vasculature of the arm or the wrist 42. The first of the apparatuses performs Doppler velocimetry by attaching an ultrasound transducer 44 to the radial artery at the wrist. Data obtained by the transducer are transferred to a Doppler velocimeter 46, and the data are further processed in processing unit 22, which is connected to Doppler velocimeter 46.

Another apparatus is based on the indirect measurement of the blood pressure in the radial artery. A pressure sensor 48, or an array of pressure sensors, is attached to the subject's wrist 42, over the radial artery, and is connected to an applanation tonometer 50. The applanation tonometer transfers a continuous voltage, corresponding to peripheral arterial blood pressure, to processing unit 22.

The blood pressure can also be measured invasively by placing a pressure sensor 52 mounted on a catheter in the radial artery. The data from the pressure sensor are transferred to a unit 54 which is connected to processing unit 22.

The processing unit determines, from each continuous waveform obtained, the temporal occurrence of aortic opening (point "B") and closure (point "X"). The possible range of temporal occurrences of aortic valve closure is limited by time predictive expectation windows, established around points approximated by heart-rate dependent regression equations, such as proposed by Weissler mentioned above. Potential "X" points, closer to the predicted X point, are weighted differently than those farther away.

When applicable, each method contributes to a "final", method-averaged $T_{LVE}$, which is used for the calculation of stroke volume and other cardiodynamic parameters relying on $T_{LVE}$. Depending on subject 10 under measurement, and his/her state of health, the various methods will not necessarily perform with the same degree of accuracy and reliability. The ability of a method to determine aortic valve opening and, especially, aortic valve closure, depends on the signal quality of the waveforms obtained. Thus, the preferred embodiment weights the $T_{LVE}$ contributions corresponding to each signal quality.

The "final" $T_{LVE}$ is displayed on a display and control panel 56 which at the same time serves for controlling the whole system.

In the preferred embodiment, the different units for processing the data, i.e., electrical bioimpedance analyzer 20 and 40, Doppler velocimeters 26 and 46, pulse oximeter 34, and applanation tonometer 50 are incorporated into a single device together with processing unit 22 and display and control panel 56. This single device is indicated at 58 and represented by a dashed line. Electrical bioimpedance analyzers 20 and 40 may be of similar design, and Doppler velocimeters 26 and 46 may be of similar design, too, or used alternatively for the esophageal or radial artery approach. Only those parts of the systems which are applied to subject 10 can, of course, not be implemented in device 58. However, the device 58 is provided with interfaces for each of the measuring devices 14, 16, 24, 30/32, 38, 44, 48, and 52/54.

Figure 2:
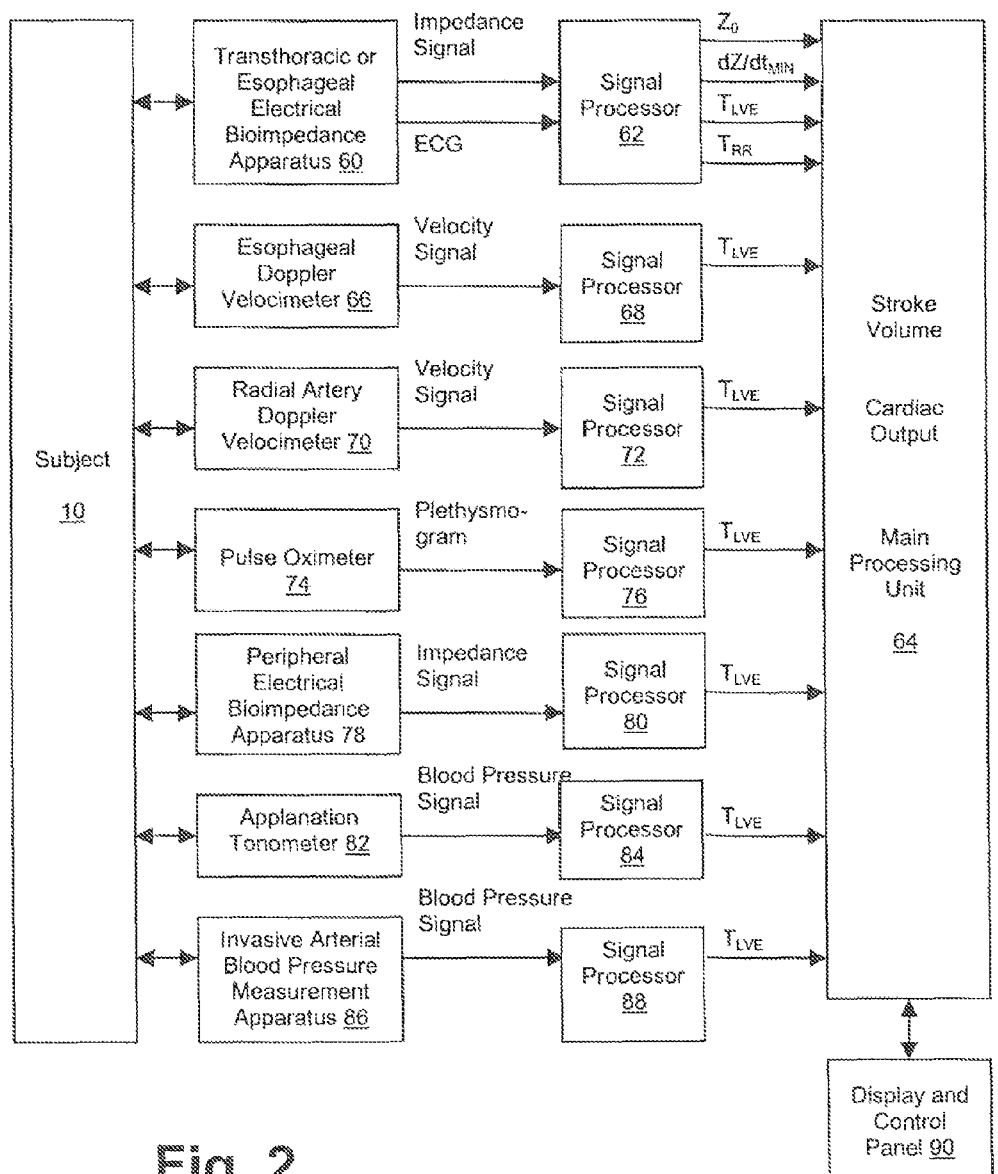
FIG. 2 schematically shows an alternative system/apparatus according to another embodiment of the present invention.

Whilst in FIG. 1, an embodiment is shown in which all possible units are part of a single device 58, FIG. 2 schematically shows how $T_{LVE}$ can be obtained by using various methods and merged into a most reliable, "final" $T_{LVE}$ determination. In particular, FIG. 2 shows a system of different apparatuses which need not necessarily be incorporated into a single device.

The system comprises a trans-thoracic or esophageal bioimpedance apparatus 60. In the context of this application, and in particular also in the claims, "thoracic electrical bioimpedance", or TEB, is not limited to the transthoracic approach using surface electrodes, but includes the application of measuring electrical bioimpedance or bioadmittance within the esophagus. Therefore, apparatus 60 is shown as a single apparatus 60 which can be considered as a first apparatus for measuring thoracic electrical bioimpedance. Bioimpedance apparatus 60 can be replaced by a bioadmittance apparatus. The TEB apparatus 60 transfers an impedance signal to a signal processor 62. At the same time, an electrocardiogram (ECG) can be obtained by apparatus 60 which is also transferred to signal processor 62. Signal processor 62 processes these data and determines a part of $Z_0$ of the impedance signal which does not change during one heart stroke, the time-derivation dZ/dt and in particular the minimum $dZ/dt_{MIN}$ of the derivation, the left-ventricular ejection time $T_{LVE}$ and the period $T_{RR}$, i.e., the time between two peaks in the ECG. All these data are transferred to a main processing unit 64.

TEB apparatus 60 is needed in all embodiments of systems according to the invention.

The system according to the invention includes at least one second apparatus selected from the group of apparatuses described in the following.

A first of these additional apparatuses is an esophageal Doppler velocimeter 66 which transfers a velocity signal to a signal processor 68 which derives a value of $T_{LVE}$ from the velocity signal and transfers this value to main processing unit 64.

Alternatively, or in addition, a radial artery Doppler velocimeter 70 can be used which transfers a velocity signal to a signal processor 72 which derives a value of $T_{LVE}$ from the velocity signal and transfers this value to main processing unit 64.

Furthermore, a pulse oximeter 74 can be provided which transfers a plethysmogram to a signal processor 76. The signal processor 76 derives a value of $T_{LVE}$ from the plethysmogram and transfers this value to main processing unit 64.

Moreover, a peripheral electrical bioimpedance 78 can be used to derive an impedance signal which is transferred to a signal processor 80, which determines a value of $T_{LVE}$ from said impedance signal and transfers it to main processing unit 64.

Another possibility is the use of an applanation tonometer 82 sending a blood pressure signal to a signal processor 84. Signal processor 84 determines a value of $T_{LVE}$ from said blood pressure signal and transfers it to main processing unit 64.

Instead of an applanation tonometer, or in addition thereto, an invasive arterial blood pressure measurement apparatus 86 can be used which transfers a blood pressure signal to a signal processor 88, the latter also deriving a value of $T_{LVE}$ from the blood pressure signal. Main processing unit 64 determines the "method-averaged", or "final" $T_{LVE}$, based on the $T_{LVE}$ measurements of the various available methods, and their signal quality. The $T_{LVE}$ measurement provided by a method with questionable signal quality will be considered with less statistical weighting than the $T_{LVE}$ measurement provided by a method with acceptable signal quality. For each method, a preferably adaptive time-predictive, expectation window may or may not be applied.

The "final" $T_{LVE}$ is used to determine the stroke volume. According to a preferred embodiment, the stroke volume is calculated by using the following formula:

$$SV = V_{EFF} \cdot \sqrt{\frac{\left|\left(\frac{dZ(t)}{dt}\right)_{MIN}\right|}{Z_0}} \cdot \frac{T_{LVE}}{\sqrt{T_{RR}}},$$

wherein $V_{EFF}$ is the effective volume of electrical participating thoracic tissue. When $V_{EFF}$ is given in milliliters, the stroke volume SV is also obtained in milliliters. This formula has been presented for the first time in the application Ser. No. 09/824,942 (Bernstein/Osypka) mentioned and incorporated above. The cardiac output is the stroke volume, multiplied with the heart rate.

The values finally obtained by main processing unit 64 are output to a display and control panel 90.

Figure 3:
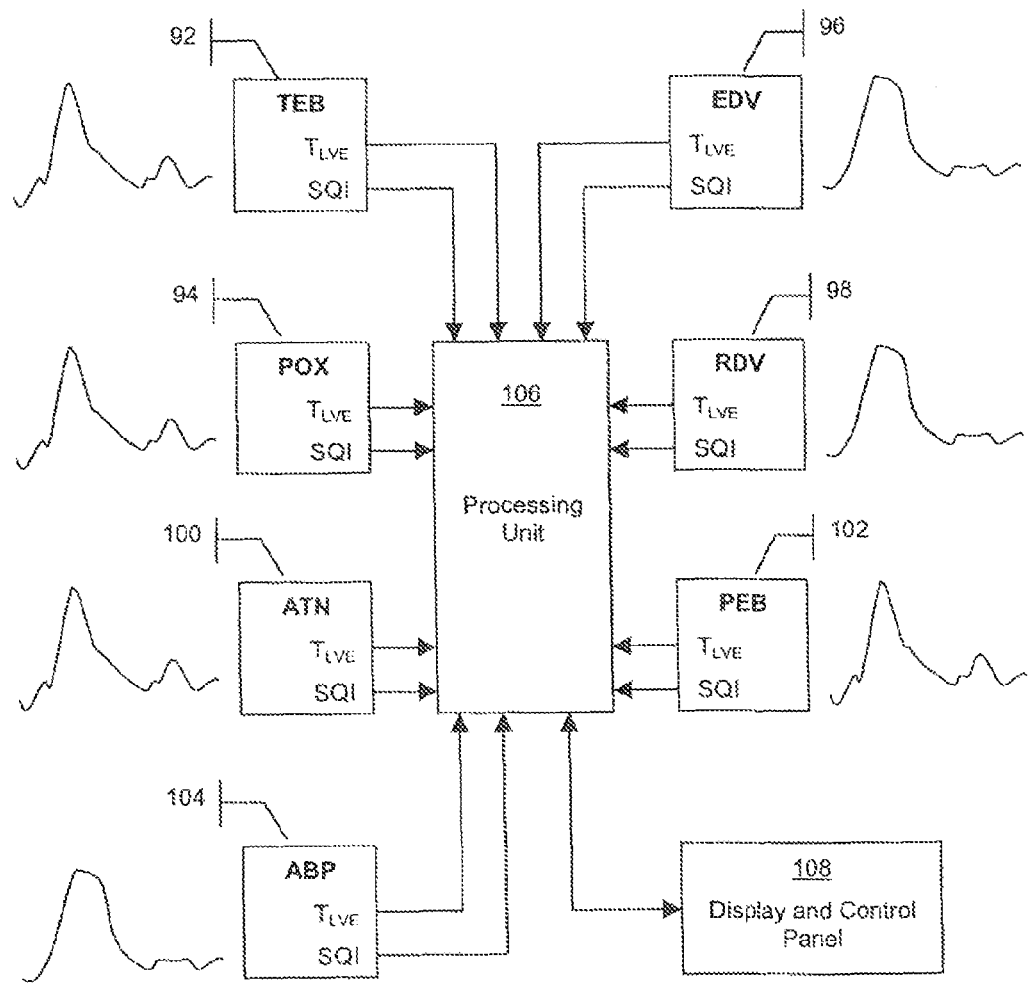
FIG. 3 illustrates the processing of waveform data obtained by various methods for determining a method-averaged $T_{LVE}$ of increased accuracy.

FIG. 3 illustrates the processing of waveform data obtained by various methods for determining a method-averaged $T_{LVE}$ of increased accuracy for computation of stroke volume and other cardiodynamic parameters relying on $T_{LVE}$.

The "final", method-averaged $T_{LVE}$ can be obtained by, but is not limited to, transferring the results of the various $T_{LVE}$ measurements through decision-node logic or a neural network. U.S. Pat. No. 6,186,955 describes a method employing a neural network to optimize determination of cardiac output. In a similar manner, waveform data recorded by a method measuring blood flow or blood pressure, or a combination thereof, such as thoracic electrical bioimpedance (TEB) 92, or bioadmittance, pulse oximetry (POX) 94, Doppler velocimetry (EDV 96 and RDV 98), applanation tonometry (ATN) 100, peripheral electrical bioimpedance (PEB) 102, or bioadmittance, or invasively measured arterial blood pressure (ABP) 104, are used as inputs to a neural network determining a "final", method-averaged $T_{LVE}$ of increased accuracy. In this implementation, a processing unit 106 determines the weighting factors based on the applicability and use of a method, and empirically derived criteria for signal quality (SQI=signal quality indicator). The operator can influence the decision process by enabling or disabling the method contributions, and thus the weighting, through a display and control panel 108.

In the following, the different methods for obtaining values of $T_{LVE}$ are described in detail, one after another.

The determination of $T_{LVE}$ from thoracic bioimpedance or bioadmittance is a standard method in the determination of the stroke volume (see the application of Bernstein and Osypka mentioned and incorporated by reference above).

Figure 4:
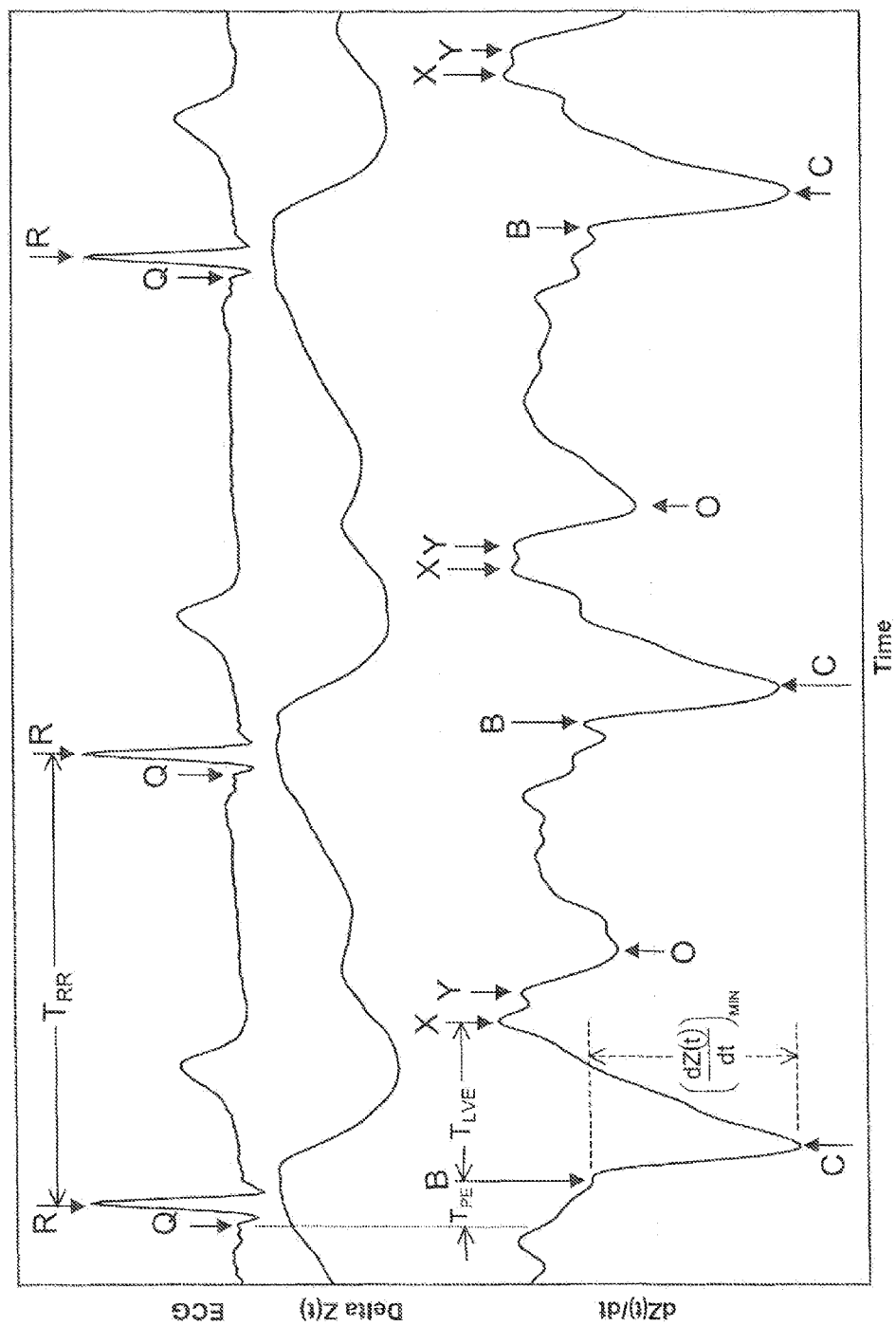
FIG. 4 illustrates parallel recordings of a surface electrocardiogram (ECG), the change in thoracic bioimpedance, $\Delta Z(t)$ ("Delta Z"), and the rate of change of bioimpedance, $dZ(t)/dt$.

FIG. 4 illustrates the parallel recordings of a surface electrocardiogram (ECG), the change in thoracic bioimpedance, $\Delta Z(t)$ ("Delta Z"), and its first time-derivative, $$\frac{dZ(t)}{dt}.$$

In the ECG, point "Q" is defined as the onset of ventricular depolarization, i.e., beginning of electrical systole.

Points "B" and "X" are characteristic points on the first time-derivative $$\frac{dZ(t)}{dt}:$$

Point "B" is indicated by a significant change in slope of the dZ(t)/dt waveform immediately preceding a strong decrease of dZ(t)/dt. This change in slope is often observed as a notch prior to the strong decrease of dZ(t)/dt up to its minimum, $$\frac{dZ(t)}{dt_{MIN}}.$$

Point "B" occurs approximately 55-65 milliseconds prior to $$\frac{dZ(t)}{dt_{MIN}}$$

and can be readily determined by using well-known methods of waveform analysis using a microprocessor or computer.

Point "X" is the next maximum in the dZ(t)/dt waveform following $$\frac{dZ(t)}{dt_{MIN}}$$

and can be readily determined by using well-known methods of waveform analysis using a microprocessor or computer.

Point "B" is defined as the opening of aortic valve and marks the beginning of the ejection phase of left-ventricular systole.

Point "X" is defined as the closure of aortic valve and marks the end of the ejection phase of left-ventricular systole.

Accordingly, the left-ventricular ejection time is defined as the time interval between point "B" and point "X".

Point "Y" is defined as the closure of the pulmonic valve, i.e., point "Y" marks the endpoint of right-ventricular systole. In a subject with anatomically normal intracardiac electrical conduction pathways (without presence of a left bundle branch block), point "Y" follows point "X" in time. The "O" wave in the $$\frac{dZ(t)}{dt}$$

waveform corresponds to rapid ventricular filling in early diastole. The time interval between point "Q" and point "B" is known as the pre-ejection period ($T_{PE}$).

Figure 5:
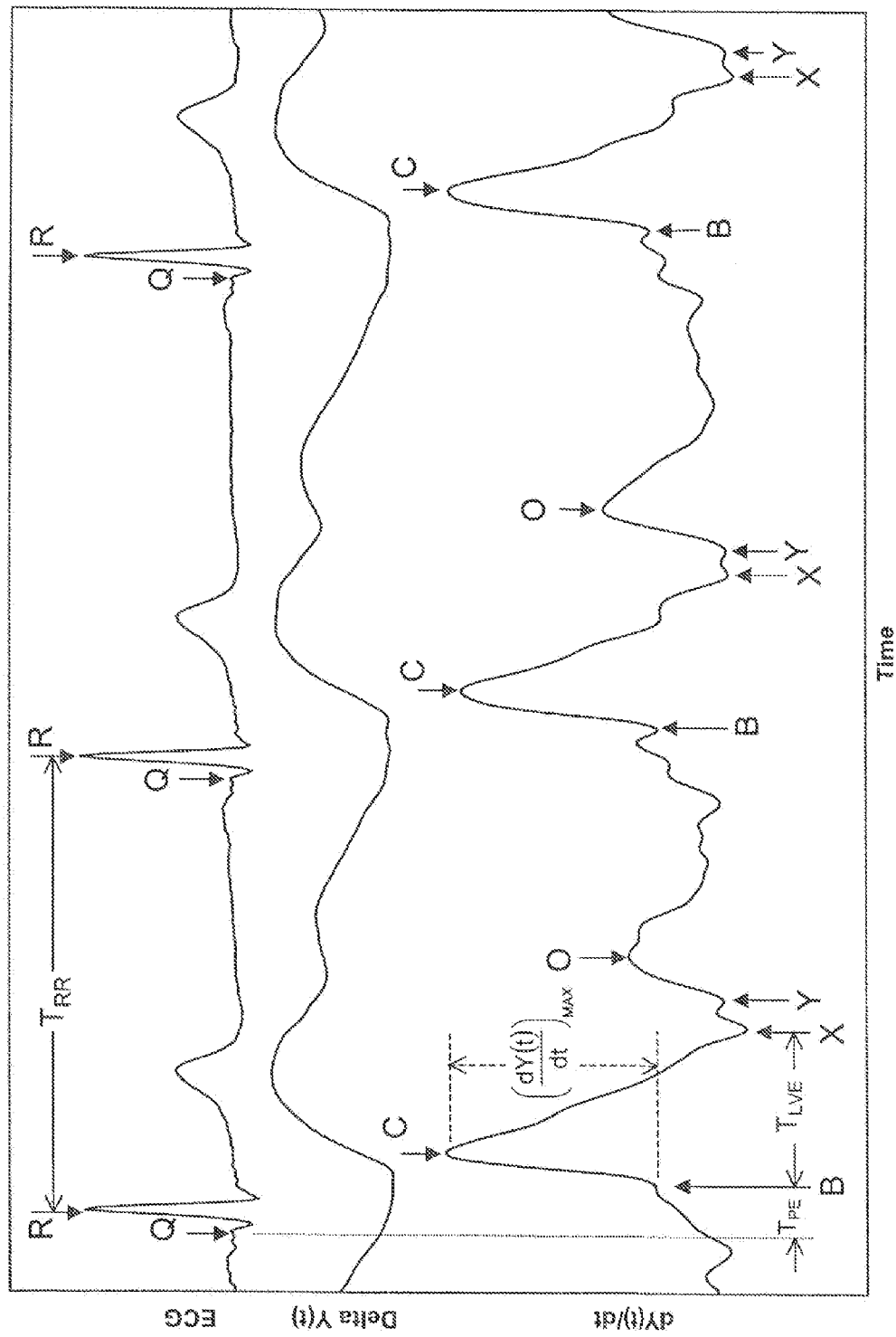
FIG. 5 illustrates parallel recordings of a surface electrocardiogram (ECG), the change in thoracic bioadmittance, $\Delta Y(t)$ ("Delta Y"), and the rate of change of bioadmittance, $dY(t)/dt$.

FIG. 5 illustrates the parallel recordings of a surface electrocardiogram (ECG), the change in thoracic admittance, $\Delta Y(t)$ ("Delta Y"), and its first time-derivative, $$\frac{dY(t)}{dt}.$$

Points "Q", "B", "X" and "O" are equivalent to FIG. 4, and, consequently, $T_{LVE}$ and $T_{PE}$.

Figure 6:
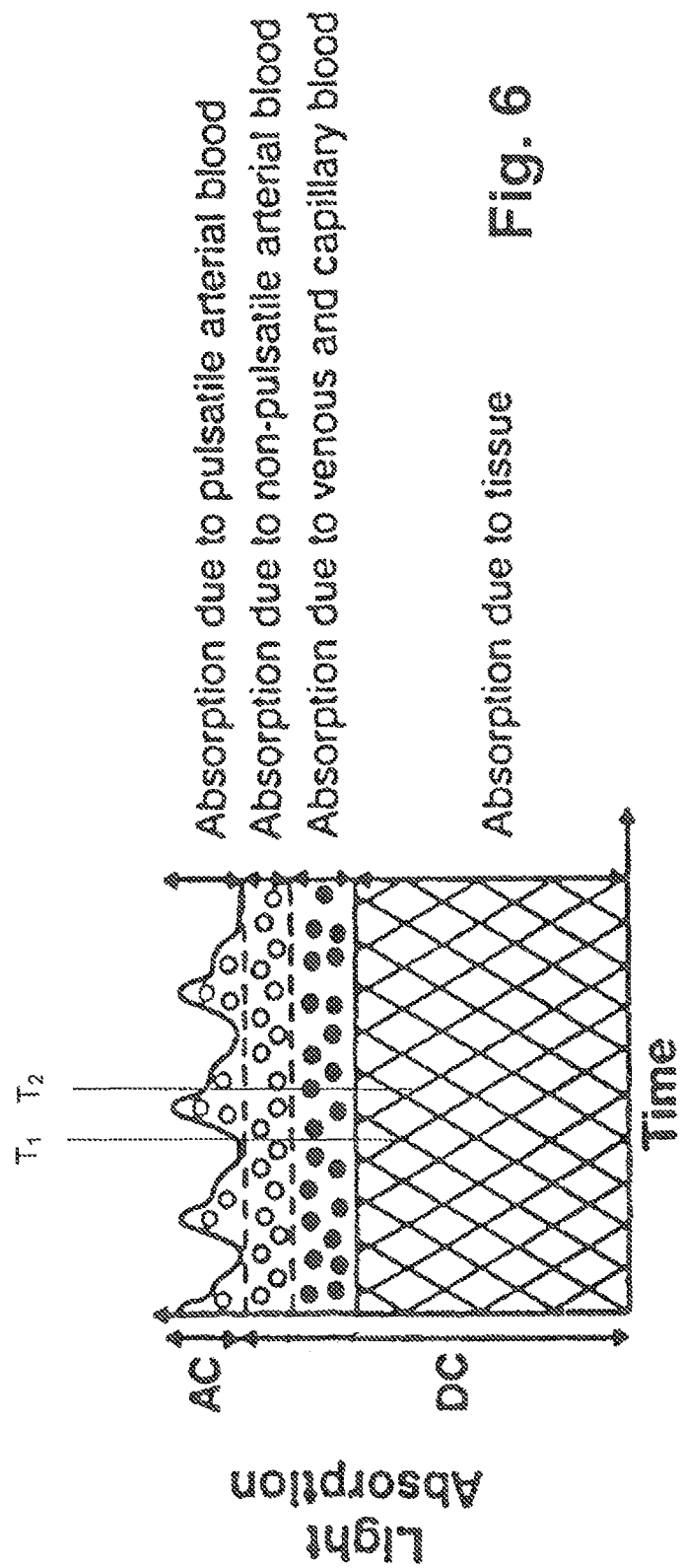
FIG. 6 illustrates light absorbance in living tissue.

With respect to pulse oximetry, FIG. 6 illustrates light absorbance in living tissue. The baseline, static component (analog to DC) represents absorbance of the tissue bed, venous blood, capillary blood, and non-pulsatile arterial blood. The pulsatile component (analog to AC) is due solely to pulsatile arterial blood.

In pulse oximetry, light is sent through living tissue (target tissue), and the light absorbance in that tissue is detected. Pulse oximeters utilize two wavelengths of light, one in the red band, usually 660 nm, and one in the infrared band, usually 940 nm. Light emitting diodes in the signal probe located at one side of the target tissue (usually the finger) emit light of the appropriate wavelength. The intensity of the light transmitted through the tissue is measured by a photo-detector located on the opposite side. Transmitted light intensities of each wavelength are sampled hundreds of times per pulse cycle. The variation in absorption of light that is sensed as the blood vessels expand and contract with each arterial pressure pulse is registered.

As arterial blood pulses in the fingertip, the path length of light increases slightly. This increase in path length and light absorption is due solely to the augmented quantity of hemoglobin in arterial blood. Hence, pulse oximetry is a non-invasive method for determining the saturation of red blood cell hemoglobin with oxygen. Since this saturation is directly related to the heart stroke, the temporal interval between opening and closure of aortic valve, $T_{LVE}$, can be derived from a plethysmogram obtained by pulse oximetry.

In pulse oximetry, it is assumed that the only pulsatile absorbance between the light source and photo detector is the arterial blood. The oximeter first determines the AC component of the absorbance at each wavelength and then divides this AC component by the corresponding DC component to derive "pulse added" absorbance hat is independent of the incident light intensity. It then calculates the ratio $$R = \frac{AC_{660}/DC_{660}}{AC_{940}/DC_{940}}.$$

The pulsatile waveform of the AC component takes the shape of an attenuated arterial pressure pulse tracing.

Figure 7:
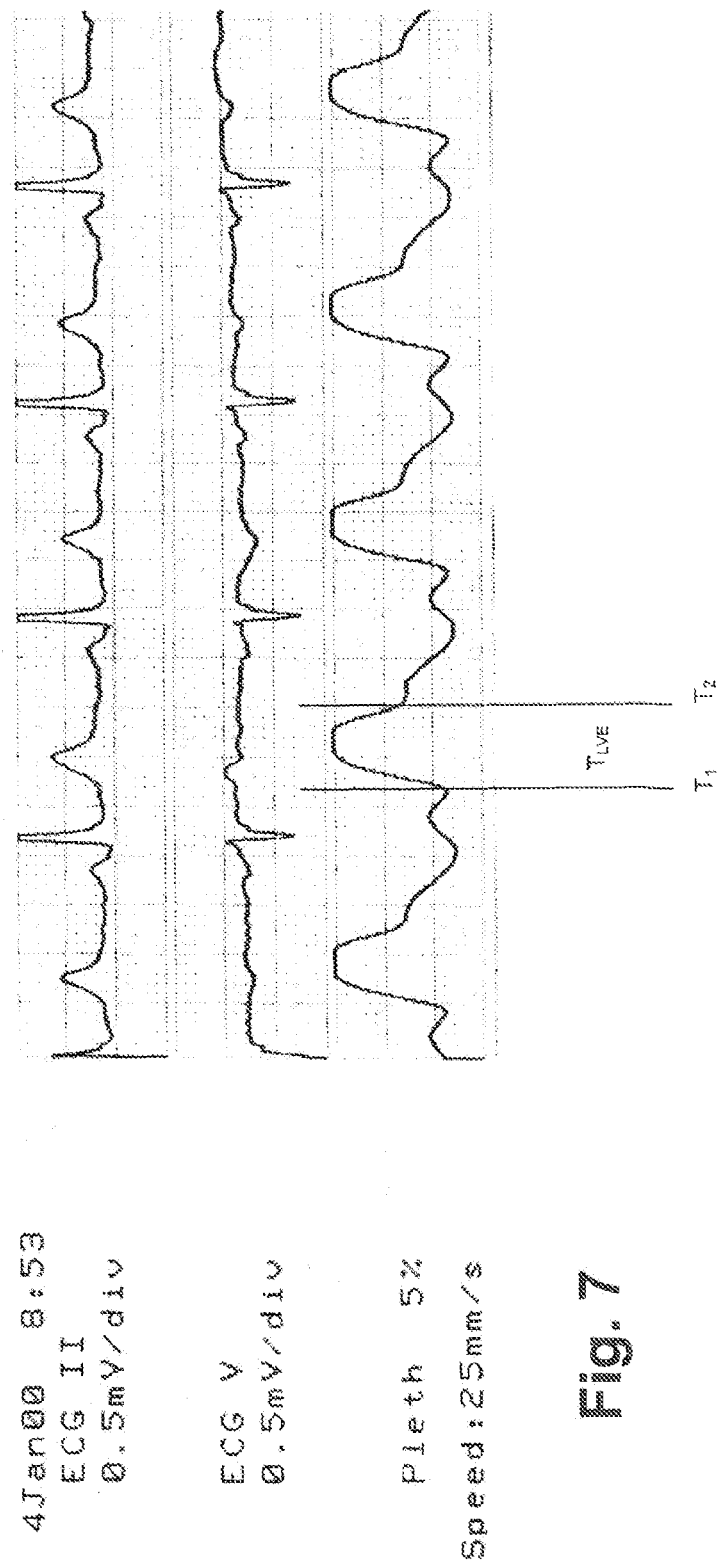
FIG. 7 illustrates a pulse plethysmogram obtained by pulse oximetry.

FIG. 7 shows three waveforms, wherein the waveform shown at the bottom is a pulse plethysmogram obtained by pulse oximetry, and wherein the two other curves are electrocardiograms shown for comparison. Of that waveform, two points $T_1$ and $T_2$ are indicated. $T_1$ is the foot of a strong upslope and corresponds to a local minimum in the plethysmogram which can be readily determined by using well-known methods of waveform analysis using microprocessors or computers. $T_2$ is the dicrotic notch equivalent on the deceleration phase of the signal. $T_2$ can be readily determined by searching for an abrupt change in the derivative of the plethysmogram by using well-known waveform analysis methods.

The time interval between $T_1$ and $T_2$ corresponds to the time interval between points "B" and "X" on the bioimpedance waveform. Thus, it is precisely equivalent to the temporal interval between opening and Closure of aortic valve ($T_{LVE}$), except for a transit time delay of the propagated arterial pressure/flow pulse wave measured from proximal to distal sampling site. The time delay ($\Delta T$) is dependent on the distance between aortic root and pulse oximetry sampling location, and on the 'stiffness" of the arterial system. $\Delta T$, however, has no effect on $T_{LVE}$.

While prior art utilizes the method of pulse oximetry determining the saturation of red blood cell hemoglobin with oxygen, a plethysmogram, as shown in FIG. 7, is used for other purposes than display. Commonly, a microprocessor or computer analysis determines the maximal oxygen saturation level and the heart rate. The determination of $T_{LVE}$ from a plethysmogram obtained by pulse oximetry, however, is not known in prior art.

An alternative or additional method to obtain a value of $T_{LVE}$ is Doppler velocimetry. Doppler velocimetry makes use of the Doppler principle. According to the Doppler principle, the frequency of waves emitted by a moving object is dependent on the velocity of that object. In Doppler velocimetry, an ultrasonic wave of constant magnitude (in the MHz range) is emitted into the axial direction of an artery comprising red blood cells which correspond to the above-mentioned moving object. The ultrasonic wave is reflected by the red blood cells (back-scattered) and the reflected wave is detected. Depending on the velocity of the red blood cells, the frequency of the reflected ultrasound is altered. The difference in frequency between the ultrasound emitted ($f_O$) and that received ($f_R$) by the Doppler transducer produces a frequency shift $$\Delta f = f_R - f_O.$$

This instantaneous frequency shift depends upon the magnitude of the instantaneous velocity of the reflected targets, their direction with respect to the Doppler transducer, and the cosine of the angle at which the emitted ultrasound intersects with the targets. The instantaneous frequency shift ($\Delta f_i$) is, like velocity, a vector, since it possesses the characteristics of both magnitude and direction. Instantaneous red blood cell velocity ($v_i$) and the corresponding Doppler frequency shift ($\Delta f_i$) are related by the Doppler equation, which is given as:

$$\Delta f_i = \frac{2 \cdot f_0 \cdot \cos\theta}{c} \cdot v_i,$$

where $\Delta f_i$ is the instantaneous frequency shift (measured in KHz), $f_0$ is the emitted, constant magnitude ultrasonic frequency (measured in MHz), c is the speed (propagation velocity) of ultrasound in tissue (blood), usually in the range of 1540-1570 m/s, θ is the incident angle formed by the axial flow of red blood cells and the emitted ultrasonic signal, and wherein $v_i$ is the instantaneous red blood cell velocity within the scope of the interrogating ultrasonic perimeter or target volume.

By algebraic rearrangement:

$$v_i = \frac{c}{2 \cdot f_0} \cdot \frac{\Delta f_i}{\cos\theta}.$$

Since c and $f_0$ are constants, $$v_i = k \cdot \frac{\Delta f_i}{\cos\theta}.$$

Moreover, if θ=0°, then cos θ=1, and then $$v_i = k \cdot \Delta f_i,$$

and $$v_i \approx \Delta f_i.$$

The system according to the preferred embodiment makes use of two different kinds of Doppler velocimeters.

Figure 8:
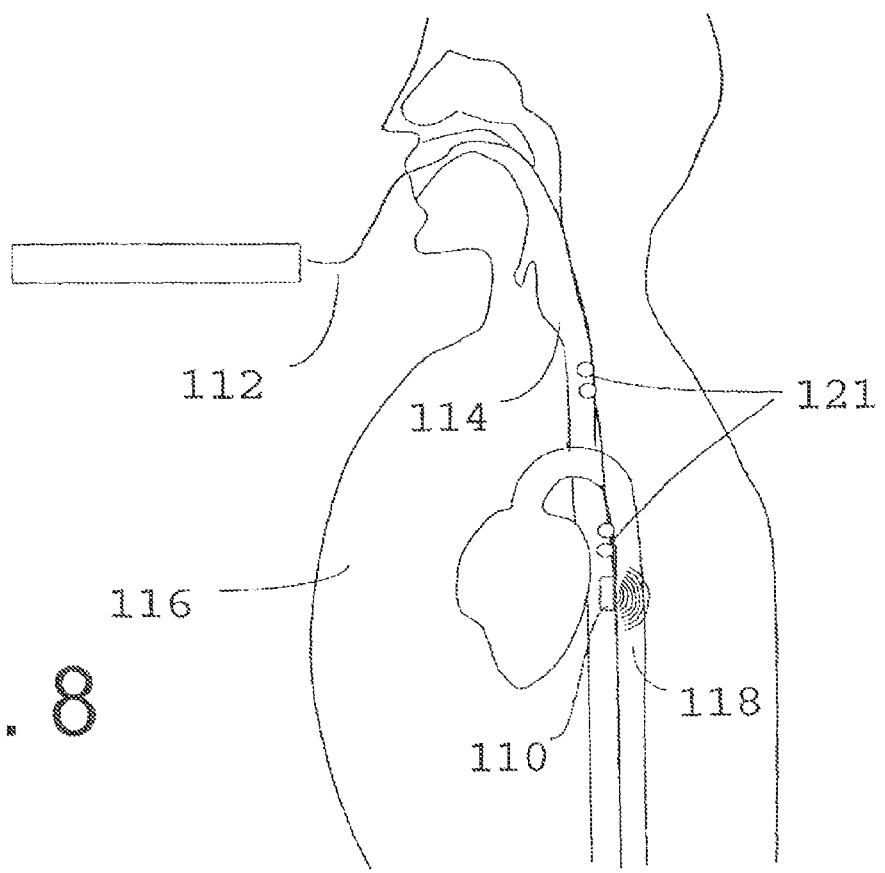
FIG. 8 illustrates how a catheter comprising electrodes for a TEB measurement and a Doppler velocimeter is placed in the human esophagus for the measurement of the left-ventricular ejection time, the left-ventricular stroke volume, and the cardiac output.

In one example, a Doppler velocimeter is placed in the human esophagus. FIG. 8 illustrates how this method is performed: A Doppler transducer 110 is affixed to the tip of a pliable plastic catheter 112 having a diameter of about 6 mm. That catheter 112 is inserted into the esophagus 114 of a subject (patient) 116. When properly aligned, the Doppler transducer senses the peak ultrasound Doppler frequency shift, proportional to peak aortic blood velocity, as well as the entire time-velocity sequence of ventricular ejection. Since the descending aorta 118 is located in close proximity to esophagus 114, Doppler transducer 110 can emit ultrasound which is reflected by blood in the aorta (indicated by the series of curves near transducer 110 in FIG. 8).

If the frequency shift $\Delta f_i$ is measured, the aortic blood flow velocity can be derived according to the formula discussed above. FIG. 9a shows a signal obtained by esophageal Doppler velocimetry. FIG. 9b shows the signal of FIG. 9a after smoothing. $T_{LVE}$ can be determined by defining the point $T_1$ when the aortic blood flow velocity starts to exceed the value of zero, and by defining the point $T_2$ when the aortic blood flow velocity again reaches a value of zero in the smoothed curve. The esophageal Doppler velocimetry is ideally suited for measurement of $T_{LVE}$ because of the close proximity of sensor 110 to descending aorta 118.

If the aortic valve cross-sectional area (CSA) is known, either by echocardiographic measurement, or by nomogram, integration of the time-velocity signal produces SV when the integral of velocity and CSA are multiplied. SV can be calculated as the product of CSA and the systolic velocity integral, known as SVI, obtained at the site of maximum flow amplitude.

According to an alternative Doppler velocimetry method, a Doppler velocimeter transducer is placed over the radial artery. This method is known in the prior art and is used in order to obtain information about the total blood flow through the radial artery. However, usually no waveforms are derived from such a measurement.

Figure 10:
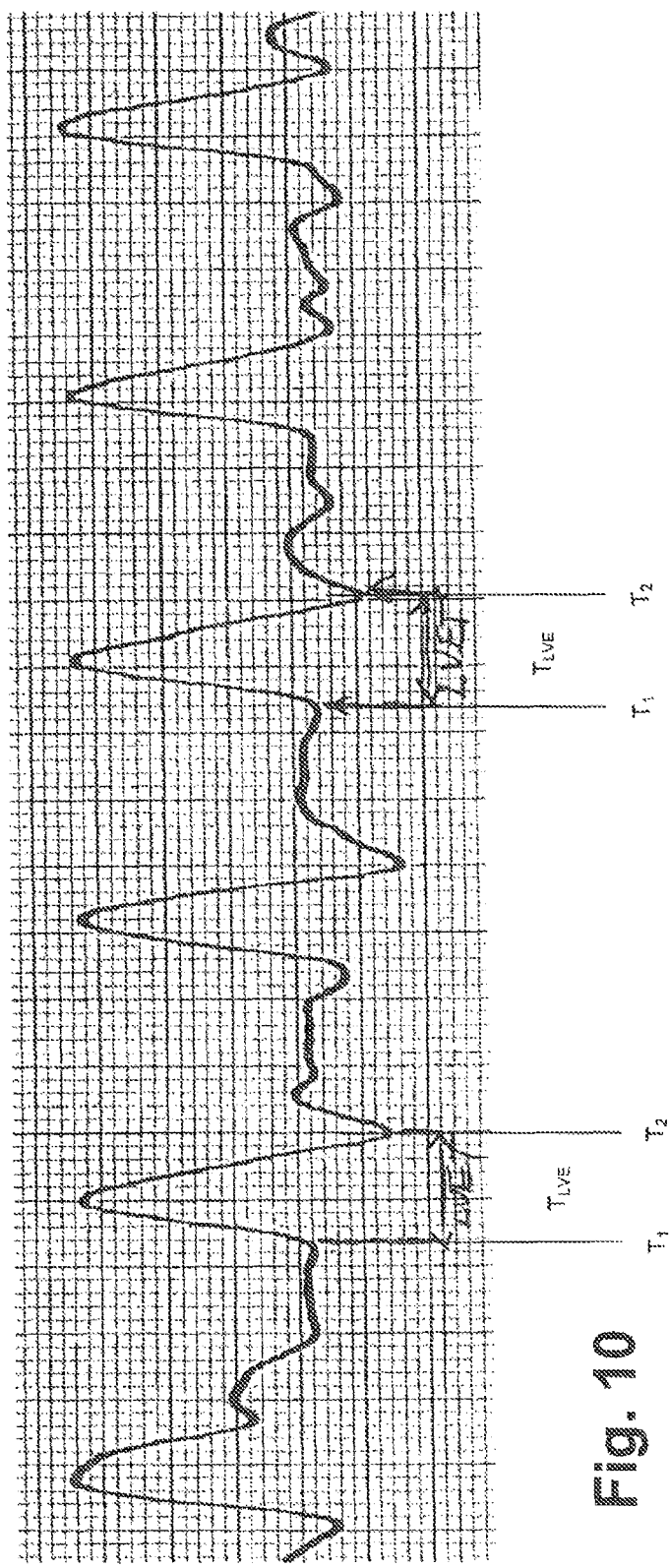
FIG. 10 shows a curve obtained by a Doppler velocimeter transducer placed over the radial artery.

However, such a waveform can readily be derived. FIG. 10 illustrates such a waveform representing the velocity of flowing blood versus time. One can define a first point $T_1$ corresponding to a local minimum in the waveform preceding an upslope ending at the total maximum in a period of the curve. This local minimum can readily be determined by using well-known computer-analysis systems.

Furthermore, a second point $T_2$ can be determined which is the absolute minimum of a period of the curve following a part of the curve descending from the maximum. This point can be determined by computer analysis, too.

The time interval between $T_1$ and $T_2$ corresponds to the time interval between points "B" and "X" on the impedance or admittance waveforms. Thus, it is precisely equivalent to the temporal interval between opening and closure of aortic valve ($T_{LVE}$), except for a transit time delay of the propagated arterial pressure/flow pulse wave measured from proximal to distal sampling site.

The pulsatile changes in the periphery follow the pulsatile changes in the aorta by a time delay ($\Delta T$), which is dependent on the distance between aortic root and sampling location on the radial artery at the wrist, and on the 'stiffness" the arterial system. $\Delta T$, however, has no effect on $T_{LVE}$.

According to an alternative, or additional, method of determining $T_{LVE}$, the arterial blood pressure is measured. Noninvasive or invasive methods can be used therefore.

Arterial tonometry (a special form of sphygmocardiography) is a technique employed to measure arterial blood pressure noninvasively. A tonometric instrument provides a continuous measurement of blood pressure, as well as registering the sensed waveform. Its continuous nature is thus akin to direct, invasive blood pressure methods. Like its invasive counterpart, arterial tonometry is usually applied to the radial artery. Tonometric measurements require a superficial artery close to an underlying bone. The radial artery is most commonly used because it is easily accessible, closely apposed to bone, and the transducer can be easily stabilized at the wrist.

Applanation tonometry typically involves a transducer, including one or more pressure sensors positioned over a superficial artery. The radial artery at the wrist is a preferred superficial artery. Manual or mechanical hands-off affixation methods provide steady pressure application to the transducer, so as to flatten (applanate) the wall of the underlying artery without occluding it. The pressure measured by the sensor is dependent upon the applied affixation pressure used to transfix the transducer against the skin of the patient, and on the arterial blood pressure transducer component, which is ideally aligned perpendicular to the axial flow of arterial blood.

Tonometric systems measure a reference pressure directly from the wrist and correlate this with arterial pressure. The tonometer sensor continuously transduces the arterial pressure pulse from systolic expansion and deceleration to aortic valve closure, and through diastolic decay and recoil. The radial arterial waveform signal is registered.

Figure 11:
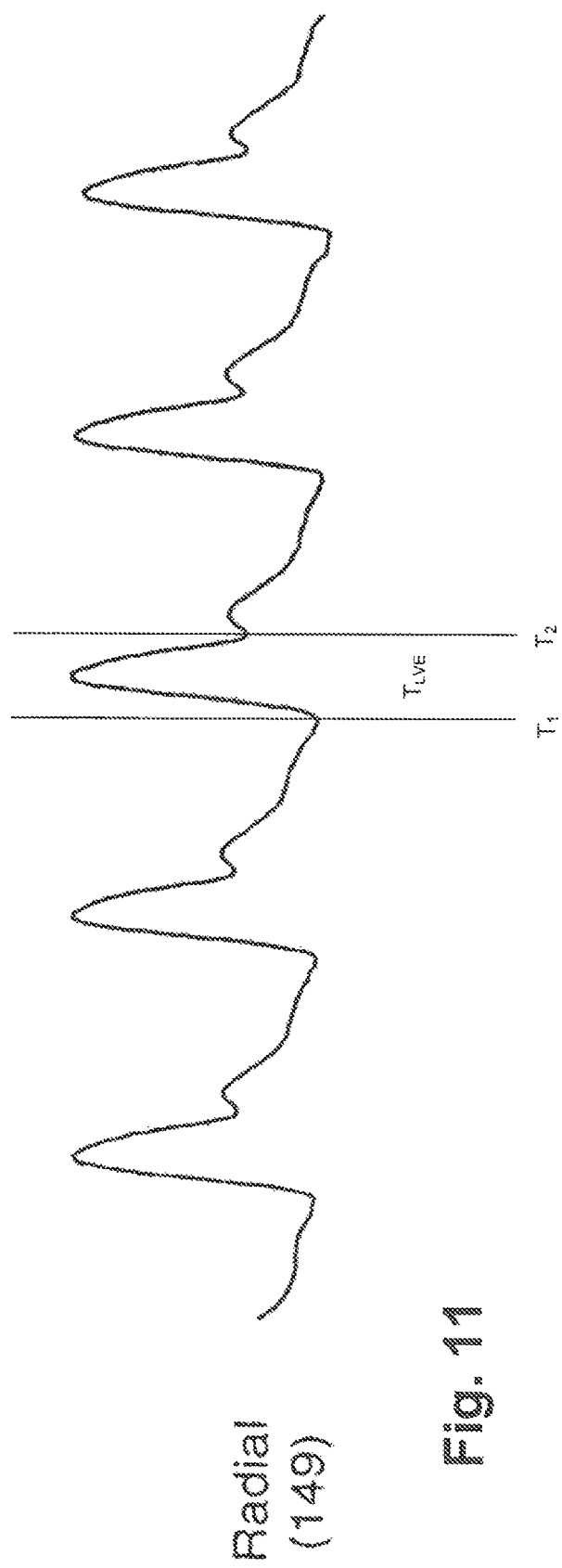
FIG. 11 demonstrates that the morphology of a velocity-versus-time wave derived from radial artery applanation tonometry is akin to an invasively derived pressure waveform.

FIG. 11 illustrates a waveform derived from radial artery applanation tonometry, i.e., a representation of the measured blood pressure versus time. In FIG. 11, the first point $T_1$ is defined where a minimum of the waveform occurs, followed by a steep upslope of the signal. This minimum can be readily determined by using computer analysis. The minimum is followed by an upslope to a maximum, and afterwards the curve is descending again and reaches a first minimum in which the point $T_2$ is defined. Such a minimum can readily be determined by using computer methods for waveform analysis. The time interval between $T_1$ and $T_2$ corresponds to the time interval between points "B" and "X" on the admittance waveform. Thus, it is precisely equivalent to the temporal interval between opening and closure of aortic valve ($T_{LVE}$), except for a transit time delay of the propagated arterial pressure/flow pulse wave measured from proximal to distal sampling site.

The pressure changes in the periphery follow the pressure changes in the aorta by a delay ($\Delta T$), which is dependent on the distance between aortic root and tonometric sampling location and on the 'stiffness" of the arterial system. $\Delta T$, however, has no effect on $T_{LVE}$.

The measurement of the radial arterial blood pressure can also be determined invasively. An invasive arterial pressure tracing is extracted by cannulation of the radial artery. A transducer connected by a fluid column provides a continuous pressure waveform that is used to determine the approximate arterial pressure. It is assumed that proper zeroing and calibration of the transducer has been effected.

When the clinical situation dictates the need for accurate, continuous blood pressure measurement, as well as frequent blood sampling for arterial blood gas analysis, cannulation of the femoral, brachial, and especially the radial artery is common.

Figure 12:
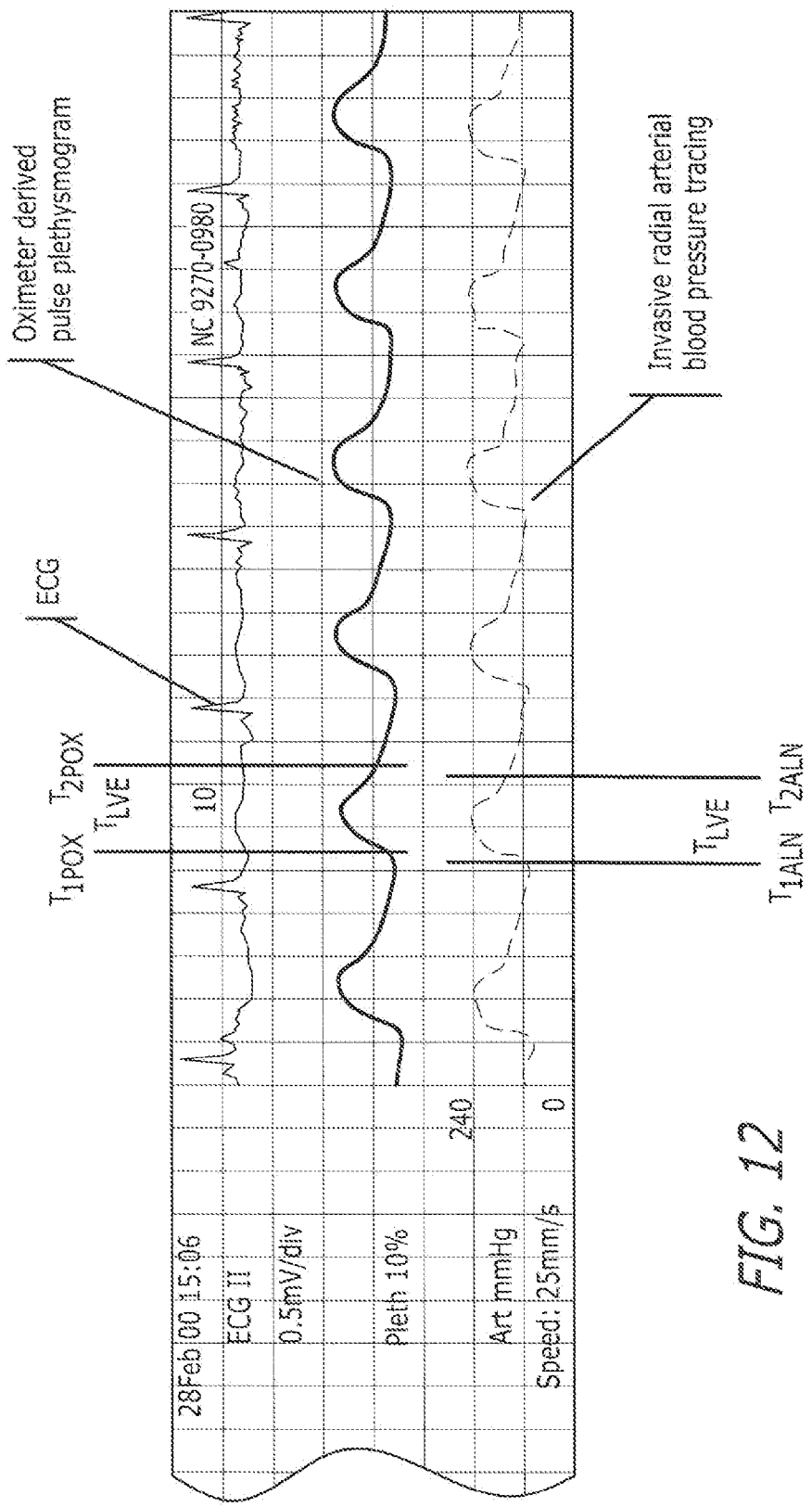
FIG. 12 demonstrates waveform tracings derived from the ECG, oximeter derived pulse plethysmogram, and invasive radial arterial blood pressure, respectively.

FIG. 12 illustrates a tracing obtained by invasive radial arterial blood pressure (curve on the bottom). For comparison, an oximeter-derived pulse plethysmogram (in the middle) and an electrocardiogram (ECG) are also shown. In a similar manner as in the case of FIG. 11, in the blood pressure tracing of FIG. 12, a first point $T_{1ALN}$ is defined as a local minimum of the waveform, preceding by steep increase of the pressure waveform. A second point $T_{2ALN}$ is defined as significant change in slope following the absolute maximum of the plethysmogram. Both points can be readily determined by using computer waveform analysis. Also shown are the two points $T_{1POX}$ and $T_{2POX}$, which have been determined in the same manner as described above with respect to FIG. 7.

It is to be noted that the time interval on the oximeter tracing $T_{1POX}$ to $T_{2POX}$ is equivalent to the time interval derived from the invasive pressure tracing, $T_{1ALN}$ to $T_{2ALN}$. Both modalities, the noninvasive and the invasive approaches, respectively, describe the same approximation of $T_{LVE}$, albeit with a temporal delay from its aortic origins.

Invasively derived blood pressure is one of the most reliable methods for the determination of $T_{LVE}$, despite that this fact is not commonly acknowledged in the prior art. The derivation of $T_{LVE}$ by means of invasively derived blood pressure can be used as a standard by which all the preceding methods are assessed.

The continuous waveforms obtained from thoracic electrical bioimpedance, or bioadmittance, esophageal Doppler velocimetry, radial artery Doppler velocimetry, pulse oximetry, applanation tonometry and invasive arterial cannulation, demonstrate, regardless of disease state, a distinct slope change upon opening of aortic valve, or equivalent upstroke of peripheral propagated pressure/flow pulse waves. However, timing of aortic valve closure, especially by waveform analysis of TEB, is sometimes obscured by the severity of the disease state, which may render this temporal landmark electronically indecipherable. Therefore, the critical determinant of $T_{LVE}$ is usually the timing of aortic valve closure. Therefore, to circumvent this problem, temporal expectation windows can be constructed by two methods: either by approximating the timely occurrence of the closure of aortic valve as predicted, or by the width of $T_{LVE}$ itself, as predicted.

TABLE 1

Regression equations for the $QS_2$ interval after Weissler et al.

| Gender | Regression equation; $[QS_2]$ in s | Standard Deviation |
|---|---|---|
| Male | $QS_2 = -0.0021 \cdot HR + 0.546$ | 0.014 s |
| Female | $QS_2 = -0.0020 \cdot HR + 0.549$ | 0.014 s |

FIGS. 13a-d illustrate the method by which a time domain is constructed for predicting the temporal occurrence of aortic valve closure. Weissler et al. (see article cited above) established regression equations for the duration of the systolic time intervals based on recordings of the electrocardiogram, phonocardiogram, and carotid arterial pulse tracing. Regarding the time domain expectation window for closure of the aortic valve, the predictive regression equation for the duration of the $QS_2$ interval is employed (Table 1). Point "Q" is defined as the onset of ventricular depolarization, i.e., beginning of electrical systole. Point "Q" can be readily determined as the local minimum in the electrocardiogram preceding the main peak in the electrocardiogram. Point '$s_2$" is defined by phonocardiography as the second heart sound and corresponds to aortic valve closure. An expectation window can be constructed by establishing temporal limits prior to and after the predicted point in time. Depending upon the timely occurrence of measured aortic valve closure, by any of the aforementioned methods, within or outside the expectation windows, an algorithmically determined nominal point of aortic valve closure is assigned. The inherent error of this approach is determined by the confidence intervals of the estimate. An alternative method for the construction of an expectation window is to establish weighted means of all timely occurrences of indicated closure points depending on the temporal distance from the predicted closure of the aortic valve.

This technique can be applied to any of the invasive and noninvasive methods described above. The closure of the aortic valve (the end of $T_{LVE}$) corresponds to the ejection phase of systole, or the end of the Q-$S_2$ time interval (electromechanical systole), determined by phonocardiography. Weissler et al. determined that Q-$S_2$ is independent of the disease state and virtually constant at any heart rate HR, while $T_{LVE}$ is highly variable. Therefore, the expectation window for $T_{LVE}$ is focused on the expected occurrence of the end of $QS_2$. The regression equations for $QS_2$, as shown in Table 1, are not applicable or valid in the presence of iatrogenically induced intraventricular conduction delay of the left bundle branch block type (i.e., single chamber ventricular pacing) or in pathologically occurring left bundle branch block.

FIGS. 14a-d illustrate the method an expectation window is established for $T_{LVE}$. Weissler et al. (see article cited above) determined the regression equations (Table 2) for systolic time intervals in normal individuals. These regression equations are not applicable for all patients categorized by certain cardiopulmonary abnormalities.

TABLE 2

Regression equations for $T_{LVE}$ after Weissler et al.

| Gender | Regression equation; $[T_{LVE}]$ in s | Standard Deviation. |
|---|---|---|
| Male | $T_{LVE} = -0.0017 \cdot HR + 0.413$ | 0.010 s |
| Female | $T_{LVE} = -0.0016 \cdot HR + 0.418$ | 0.010 s |

The user of the invention can implement one, a combination, or all, alternative aforementioned methods delineated, dictated by the clinical situation, the constraints of time, and the necessity for near absolute accuracy of stroke volume, cardiac output and systolic time ratio measurements determined by means of TEB.

Since $T_{LVE}$ is linearly and highly correlated negatively with heart rate (HR), time domains related to standard regression equations may be used to identify the time domain in which aortic valve closure is statistically expected to occur. Algorithmic decision nodes, based on static requirements and/or artificial neural networks, can determine which method, or methods, provides the most accurate assessment of $T_{LVE}$.

In each of the methods described above, the expectation window for the closure of aortic valve (see FIGS. 13a-d) or for the width of $T_{LVE}$ itself (see FIGS. 14a-d) can be useful, and those criteria used to define the points in the respective curve which are employed to determine $T_{LVE}$. By the application of the expectation windows, errors in the determination of these respective points can be considerably reduced.

If the closure of aortic valve (point "X") can be definitively be determined by signal analysis in conjunction with time windows, this interval will be entered into computation.

If signal failure occurs, such that no alternative method can provide accurate $T_{LVE}$ measurements, the invention will default to standard regression equations, and/or alert the user of inappropriate signal quality. In the rare case that the alternative methods fail to provide precise $T_{LVE}$ measurements, the invention can default to $T_{LVE}$ determined by means of TEB.

Though the system according to the invention has been described to include apparatuses for employing a plurality of alternative methods, those systems will fall under the scope of the invention in which the TEB apparatus for determining $T_{LVE}$ is combined with at least a second apparatus. Preferably three out of the alternative methods discussed above are implemented in a system according to the invention. The specific system used may be dependent upon the specific purpose for which the system is to be used, in particular for the special field in which the medical specialists using the system works.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:
1. A system for determining the left-ventricular ejection time $T_{LVE}$ of a heart of a subject, the system comprising:
 a first apparatus for measuring data representing one of thoracic electrical bioimpedance and thoracic electrical bioadmittance over time;
 at least one second apparatus selected from the group comprising:
 an apparatus for deriving plethysmogram data, an apparatus for deriving signal data representing the velocity of blood in an artery in the vicinity of the esophagus of the subject, an apparatus for deriving signal data representing the velocity of blood in radial artery of the subject, a first pressure sensor configured to be non-invasively attached to the subject, said first pressure sensor for measuring data representing the blood pressure in an artery of the subject, a second pressure sensor configured to be inserted into an artery of the subject, said second pressure sensor for measuring data representing the blood pressure in an artery of the subject, an apparatus for measuring data representing peripheral electrical bioimpedance, and an apparatus for measuring data representing peripheral electrical bioadmittance; and a device configured to input and derive from the data obtained by said first apparatus and said at least one second apparatus an averaged opening point of the aortic valve by averaging valve opening time-points measured by said first apparatus and said at least one second apparatus using predetermined criteria, and further configured to input and derive from the data obtained by said first apparatus and said at least one second apparatus an averaged closure point of the aortic valve by averaging valve closing time-points measured by said first apparatus and said at least one second apparatus using the predetermined criteria, and further configured to determine a value for $T_{LVE}$ by calculating the time interval between the averaged opening point of the aortic valve and the averaged closure point of the aortic valve.

2. The system according to claim 1, further comprising:

a device communicating with said first apparatus using the predetermined criteria to independently define the opening and the closure points of the aortic valve of the subject based on the data obtained by said first apparatus, and for each of said at least one second apparatus selected from the group, a device communicating with said at least one second apparatus using the predetermined criteria to independently define the opening and the closure points of the aortic valve of the subject based on the data obtained by said at least one second apparatus.

3. A system according to claim 2, wherein said device adapted to input, derive, and determine, said device communicating with said first apparatus, and said device communicating with said at least one second apparatus are formed as a unit.

4. The system according to claim 1, further comprising at least one of a display for displaying the value of $T_{LVE}$ determined by said system and an output line for electronically outputting the value of $T_{LVE}$ determined by said system.

5. The system according to claim 1, wherein the predetermined criteria includes weighted values for valve opening time-points and valve closing time-points.

6. The system according to claim 1, wherein said first apparatus comprises: at least two electrodes attached to the subject; an alternating current (AC) source connected to said at least two electrodes and applied to the subject; a voltmeter adapted to measure a voltage drop across the subject.

7. The system according to claim 6, wherein said electrodes are adapted to attach to the thorax of the subject.

8. The system according to claim 6, further comprising a catheter adapted to be inserted in the esophagus of the subject, wherein said electrodes are placed on said catheter.

* * * * *